United States Patent
Benage et al.

(12)

(10) Patent No.: US 6,274,683 B1
(45) Date of Patent: Aug. 14, 2001

(54) TEST METHOD FOR EVALUATING SOLUBLE POLYMER GROWTH WHEN RECYCLING INHIBITOR STREAMS

(75) Inventors: Brigitte Benage, Wolcott; Brendan J. Geelan, East Haven; Gerald J. Abruscato, Southington, all of CT (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 0 days.

(21) Appl. No.: 09/345,231

(22) Filed: Jun. 30, 1999

(51) Int. Cl.7 .......................................................... C08F 2/38
(52) U.S. Cl. .......................... 526/82; 526/59; 526/348.2; 526/82; 436/85
(58) Field of Search ............................ 526/59, 82, 348.2, 526/85; 436/85

(56) References Cited

U.S. PATENT DOCUMENTS

| | | | |
|---|---|---|---|
| 3,959,395 | 5/1976 | Higgins, Jr. et al. | 260/622 |
| 4,033,829 | 7/1977 | Higgins, Jr. et al. | 203/9 |
| 4,252,615 | 2/1981 | Watson | 203/9 |
| 4,469,558 | 9/1984 | Watson | 202/154 |
| 5,648,574 | 7/1997 | Arhancet et al. | 585/5 |
| 5,807,937 | * 9/1998 | Matyjaszewski et al. | 526/135 |
| 5,907,071 | 5/1999 | Arhancet | 585/5 |

FOREIGN PATENT DOCUMENTS 2069523   4/1979   (GB) .

OTHER PUBLICATIONS

Experimental Methods in Polymer Chemistry by Rabek, John Wiley and Sons Ltd. p. 67, 1980.*
Ivan, Macromol. Symp. 88:201–215 (1994) no month.
Shigemoto et al., Macromol. Rapid Commun. 17:347–351 (1996) no month.
Greszta et al., Macromolecules 29:7661–7670 no month.

* cited by examiner

Primary Examiner—David W. Wu
Assistant Examiner—William Cheung
(74) Attorney, Agent, or Firm—Raymond D. Thompson; Paul Grandinetti

(57) ABSTRACT

An improvement in a method for evaluating the efficiency of polymerization inhibitors is disclosed, wherein the improvement comprises:

A) producing dissolved polymer in a solution comprising monomer and at least one inhibitor by means of any test known in the art to be useful for evaluating polymerization inhibitors, B) collecting the polymer-containing solution, C) measuring the degree of polymerization of the monomer in the collected solution, and D) re-subjecting the polymer-containing solution to the test conditions of A).

6 Claims, No Drawings

TEST METHOD FOR EVALUATING SOLUBLE POLYMER GROWTH WHEN RECYCLING INHIBITOR STREAMS

BACKGROUND OF THE INVENTION

1. Field of the Invention

The present invention is directed to a test method for evaluating the effectiveness of various compounds in their ability to prevent polymer growth via a "living" polymerization mechanism when the "living" polymer is dissolved in the monomer stream.

2. Description of Related Art

Many ethylenically unsaturated monomers undesirably polymerize at various stages of their manufacture, processing, handling, storage, and use. Polymerization, such as thermal polymerization, during their purification results in the loss of the monomer, i.e., a lower yield, and an increase in the viscosity of any tars that may be produced. The processing and handling of the higher viscosity tars then requires higher temperature and work (energy cost) to remove residual monomer.

A wide variety of compounds has been proposed and used for inhibiting uncontrolled and undesired polymerization of ethylenically unsaturated monomers. However, many of these compounds have not been fully satisfactory. Accordingly, there has been a continuing need in the art for a testing means by which compositions intended for use as monomer polymerization inhibitors can be evaluated.

There are several mechanisms by which polymerization inhibitors work. One mode of action for polymerization inhibitors is for the inhibiting species to combine with the propagating polymer chain such that the polymerization of that polymer chain stops, i.e., a termination reaction. If such an inhibitor-terminated polymer chain is capable of participating in a dynamic equilibrium between a dormant species (the inhibitor-terminated chain) and an active polymer chain, it would be considered a "living" or quasiliving polymer. For example, Ivan, *Macromol. Synp.* 88:201–215 (1994) describes quasiliving polymerization as a polymerization in which ". . . only a portion of chain ends are active (propagating) and these are in equilibria with inactive (dormant, nonpropagating) chains . . . " Shigemoto et al., *Macromol. Rapid Commun.* 17:347–351 (1996) state, "Well-defined polymers can be prepared by controlled/"living" radical polymerization in the presence of relatively stable radicals. These systems employ the principle of dynamic equilibration between dormant species and growing radicals via reversible homolytic cleavage of a covalent bond in dormant species." Further, Greszta et al., *Macromolecules* 29:7661–7670 (1996) state, "The reversible homolytic cleavage of dormant species can be accomplished by either thermal, photochemical, or catalytic activation. The most successful approaches are as follows: homolytic cleavage of alkoxyamines and dithiocarbamates, use of various organometallic species, and catalyzed atom transfer radical polymerization." Such a "living" polymer is capable of increasing in molecular weight (growing) through its reaction with additional monomer units of the same or different types of polymerizable monomers.

The method by which this "living" polymer grows is termed the "living" polymerization mechanism, and is depicted below.

$$M\text{-Inh} \rightarrow M^* + {}^*\text{Inh} \tag{1}$$

$$M^* + {}^*\text{Inh} \rightarrow M\text{-Inh} \tag{2}$$

$$M^* + M' \rightarrow M\text{-}M'^* \tag{3}$$

$$M\text{-}M'^* + {}^*\text{Inh} \rightarrow M\text{-}M'\text{-Inh} \tag{4}$$

Reactions (1) and (2) depict the dynamic equilibrium, with (2) being the termination reaction. Reaction (3) depicts growth of the polymer chain. Reaction (4) depicts re-termination of the growing polymer chain with the inhibiting species. The amount of growth over any period of time is dependent on the relative rate at which (2) occurs versus (3), as long as (1) occurs to some extent. The faster (2) is relative to (3), the more time is needed for significant growth of the polymer. Under the conditions in which inhibitors are normally used, the concentration of the inhibiting species should be sufficiently high to cause reaction (2) to be much faster than reaction (3), otherwise it would not be an effective inhibiting system for commercial use. However, we have realized that even at an effective inhibiting amount of the inhibitor, growth can still occur, given sufficient time and temperature.

There are at least two scenarios in which "living" polymer can remain in a monomer purification train for an excessive amount of time.

First, the use of recycle can significantly increase the amount of time that the "living" polymer can remain in the purification train. To recycle unused inhibitor that is left in the purification stream after removal of the monomer, a portion of the residual stream is added to a feed stream earlier in the purification train. This residual stream typically contains inhibitor, small amounts of monomer, impurities in the monomer stream that have been concentrated by the purification process, and polymer formed during the purification process. Recycling this polymer will allow it time to grow if it is "living" polymer and the conditions of the purification train allow the "living" polymerization mechanism to occur. If this polymer grows via the "living" polymerization mechanism, excessive polymerization would cause loss in product yield, increased waste residues from the process, and potential plugging of equipment due to excessively high molecular weight polymer in the purification stream.

Second, occasionally, conditions in the plant/purification process can result in the formation of polymer within the purification train that is not dissolved by the monomer stream. If this polymer is caught in a deadspace, or if it attaches to the metal on the inside of the equipment, it will not be washed out of the system. Thus, the polymer will remain within the system indefinitely (potentially for two or more years). If this polymer grows via the "living" polymerization mechanism, it could coat the inside of the equipment, causing inefficient separation of the monomer stream components and/or insufficient heating of the stream to enable purification. Such a situation would cause loss in product yield and could potentially cause an unscheduled shut-down of the plant in order to clean out the undissolved polymer in the equipment. Such a shut-down results in loss of monomer production and additional expense to clean out and dispose of the undissolved polymer.

SUMMARY OF THE INVENTION

Given the potential loss in monomer yield as well as loss in monomer production and the additional economic drawbacks due to increased waste residues and cleaning of plugged equipment, a test method has now been developed to evaluate the effectiveness of various compounds in their ability to prevent polymer growth via a "living" polymerization mechanism when the "living" polymer is dissolved in the monomer stream.

This test method comprises:
A) producing polymer in solution via any test normally used to evaluate polymerization inhibitors, such as, but not limited to, static tests, dynamic tests, small scale simulations of a distillation column and/or reboiler, and pilot units for a distillation train,
B) collecting the polymer-containing solution, and
C) re-subjecting the polymer-containing solution to the test conditions.

More particularly, the present invention is directed to an improvement in a method for evaluating the efficiency of polymerization inhibitors, wherein the improvement comprises:

A) producing dissolved polymer in a solution comprising monomer and at least one inhibitor by means of any test known in the art to be useful for evaluating polymerization inhibitors,
B) collecting the polymer-containing solution,
C) measuring the degree of polymerization of the monomer in the collected solution, and
D) re-subjecting the polymer-containing solution to the test conditions of A).

DESCRIPTION OF THE PREFERRED EMBODIMENTS

As stated above, the present invention is directed to a test method that comprises:
A) producing polymer in solution via any test normally used to evaluate polymerization inhibitors, such as, but not limited to, static tests, dynamic tests, small scale simulations of a distillation column and/or reboiler, and pilot units for a distillation train,
B) collecting the polymer-containing solution, and
C) re-subjecting the polymer-containing solution to the test conditions.

Typically, fresh inhibitor is added to the polymer-containing solution in an amount that would bring the total level of inhibitor to the level charged in the initial test. The process of collecting polymer-containing solution and re-subjecting it to the reaction conditions (with additional inhibitor added) can be, and usually is, repeated several times. This is termed a "Multi-Pass Test" with each subjection to the test conditions constituting a single "pass."

The effects of each pass can be measured in many ways, including, but not limited to, measurement of the amount of polymer made during the pass, measurement of the concentration of polymer at steady-state (for dynamic tests), measurement of the induction time to polymerization (for static tests), and measurement of the molecular weight (Mw, Mn, Mz) and molecular weight distribution (MWD, Mw/Mn) of polymer made during the pass.

The advantages and the important features of the present invention will be more apparent from the following examples.

EXAMPLES

Procedure for Multi-Pass Reboiler Test
Preparation of First Pass Feed Solution:
Tert-butylcatechol (TBC) is removed from commercially available styrene by distillation under vacuum. Removal of TBC is verified by caustic titration. The desired amount of inhibitor(s) is added to this TBC-free styrene either directly or by first making a concentrated solution of the inhibitor in TBC-free styrene followed by further dilution with TBC-free styrene.

Preparation of Second and Third Pass Feed Solutions:
The Bottoms Stream from the previous Pass is collected except for the material in the Pot at the end of the run. The amounts of inhibitor(s) in the First Pass Feed Solution and the Bottoms Stream from the First Pass are determined by appropriate analytical method(s), e.g., gas chromatography. An amount of inhibitor(s) is added to the collective Bottoms Stream from the First Pass to increase the level of inhibitor (s) in the Bottoms Stream to a level equal to that found in the First Pass Feed Solution. An equivalent amount of inhibitor (s) is added to the collective Bottoms Streams for subsequent Passes.

Procedure for Reboiler Test (A Dynamic Test):
A quantity of the Feed Solution containing inhibitor (blend) at the desired charge (stated as a wt/wt total inhibitor to styrene) is added to a round-bottom flask (the Pot) and heated to the desired temperature (usually 130° C.) and brought to reflux by adjusting the pressure/vacuum. Once the Pot contents are at temperature, a continuous stream of fresh Feed Solution is begun at a rate that will add the volume of the initial Pot solution to the Pot over a period of time called the residence time (typically, one hour). At the same time that the fresh Feed Solution flow is begun, the Bottoms Stream flow is also begun. The Bottoms Stream is solution in the Pot that is removed at the same rate as the fresh Feed Solution is added. The equal flows of Feed and Bottoms Streams cause the quantity in the Pot to remain constant over the time of the experiment, while allowing continuous replenishment of inhibitor. This procedure simulates the way inhibitors are used in a distillation train of a plant producing vinyl monomers. The experiment continues with flow in and out of the Pot for a specified period of time. Typically, the First Pass runs for 10 hours, the Second Pass runs for 9 hours, the Third Pass runs for 8 hours, etc.

Samples are collected hourly from the Bottoms Stream. These samples are analyzed for polymer content via the methanol turbidity method. The amount of polymer in the samples is an indication of effectiveness of the inhibitor system being tested. "Average Polymer Make" is the average of the polymer content values for samples taken after 4 hours running. The difference in the amount of polymer made in one Pass versus subsequent Passes is an indication of the ability of the inhibiting system to prevent or allow polymer to grow. For example, an increase in the amount of polymer made going from one Pass to the next which is roughly equivalent to the amount of polymer made during the First Pass is an indication that polymer is not growing under the test conditions. Conversely, an increase in the amount of polymer made going from one Pass to the next which is dramatically greater (about 10 times or more) than the amount of polymer made during the First Pass is an indication that polymer is growing under the test conditions.

The material left in the Pot at the end of the run is quickly removed and cooled, to stop any further polymerization. The material is then concentrated, if necessary, under reduced pressure at 40° C. until the polymer content is >5 wt %. A sample of this polymer solution is then analyzed by Gel Permeation Chromatography (GPC) to determine the weighted average molecular weight ($M_w$) of the polymer. The difference in the $M_w$ of the polymer made in one Pass versus subsequent Passes is an indication of the ability of the inhibiting system to prevent or allow polymer to grow. Any significant increase in $M_w$ of the polymer made in one Pass versus the previous Pass is an indication that the polymer is growing under the test conditions.

This test is illustrated by the following examples in TABLE 1.

TABLE 1

| Inhibitor System/Pass | Average Polymer Make (wt %) | $M_w$ of Polymer |
|---|---|---|
| 300 ppm 4-oxo-2,2,6,6-tetramethyl-1-piperidinyloxy (4-oxo-TEMPO) | | |
| Pass 1 | 0.052 | 3,910 |
| Pass 2 (+150 ppm 4-oxo-TEMPO) | 1.45 | 17,000 |
| Pass 3 (+150 ppm 4-oxo-TEMPO) | 7.45 | 31,700 |
| 900 ppm PDA; 600 ppm DNBP; 7 cc/min air | | |
| Pass 1 | 0.066 | 5,160 |
| Pass 2 (+65 ppm PDA/270 ppm DNBP) | 0.183 | 5,150 |
| Pass 3 (+65 ppm PDA/270 ppm DNBP) | 0.423 | 5,740 |
| 1500 ppm DNBP | | |
| Pass 1 | 0.109 | 3,990 |
| Pass 2 (+435 ppm DNBP) | 0.266 | 4,170 |
| Pass 3 (+435 ppm DNBP) | 0.430 | 4,500 |

PDA = N-phenyl-N'-(1,4-dimethylpentyl)-para-phenylenediamine
DNBP = 2,4-dinitro-6-sec-butylphenol In view of the many changes and modifications that can be made without departing from principles underlying the invention, reference should be made to the appended claims for an understanding of the scope of the protection to be afforded the invention.

What is claimed is:

1. A test method for evaluating the effectiveness of polymerization inhibitors in their ability to prevent polymer growth via a living polymerization mechanism when the living polymer is dissolved in its monomer comprising:

A) producing dissolved polymer in a solution comprising monomer and at least one inhibitor by means of any test known in the art to be useful for evaluating polymerization inhibitors, B) collecting a first polymer-containing solution, C) measuring the degree of polymerization of the monomer in the first polymer-containing solution, D) re-subjecting the first polymer-containing solution to the test conditions of A) to produce a second polymer-containing solution, E) collecting the second polymer-containing solution, F) measuring the degree of polymerization of the monomer in the second polymer-containing solution, and G) comparing the measurements obtained in steps C) and F), whereby an indication of the ability of the polymerization inhibitor to prevent or allow polymer growth is obtained.

2. The method of claim 1 further comprising the step of adding fresh inhibitor to the solution prior to re-subjecting the polymer-containing solution to the test conditions of A).

3. The method of claim 2 wherein the fresh inhibitor is added to the polymer-containing solution in an amount sufficient to bring the total level of inhibitor to the level charged in the initial test.

4. The method of claim 1 wherein the test of step A) is selected from the group consisting of static tests, dynamic tests, small scale simulations of a distillation column and/or reboiler, and pilot units for a distillation train.

5. The method of claim 1 wherein the measurement step employs a technique selected from the group consisting of measurement of the amount of polymer made during a pass, measurement of the concentration of polymer at steady-state, measurement of the induction time to polymerization, and measurement of the molecular weight and molecular weight distribution of polymer made during a pass.

6. The method of claim 1 wherein the monomer is styrene.

* * * * *